United States Patent
Matsumura et al.

(10) Patent No.: US 9,060,737 B2
(45) Date of Patent: Jun. 23, 2015

(54) ULTRASONIC DIAGNOSTIC APPARATUS AND ULTRASONIC IMAGE DISPLAY METHOD

(75) Inventors: Takeshi Matsumura, Tokyo (JP); Toshihiko Kawano, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 1610 days.

(21) Appl. No.: 11/913,852

(22) PCT Filed: May 9, 2006

(86) PCT No.: PCT/JP2006/309290
§ 371 (c)(1),
(2), (4) Date: Jan. 15, 2009

(87) PCT Pub. No.: WO2006/121031
PCT Pub. Date: Nov. 16, 2006

(65) Prior Publication Data
US 2009/0216123 A1    Aug. 27, 2009

(30) Foreign Application Priority Data

May 9, 2005    (JP) ................................. 2005-136233

(51) Int. Cl.
*A61B 8/00* (2006.01)
*A61B 8/08* (2006.01)
(Continued)

(52) U.S. Cl.
CPC . *A61B 8/485* (2013.01); *A61B 8/08* (2013.01); *A61B 8/14* (2013.01); *G01S 7/52071* (2013.01); *G01S 7/52073* (2013.01); *G01S 7/52074* (2013.01); *G01S 7/52042* (2013.01)

(58) Field of Classification Search
CPC ...... A61B 8/485; A61B 5/0048; A61B 8/469; A61B 8/13
USPC .................. 600/407, 437, 438, 462, 466, 470
See application file for complete search history.

(56) References Cited

U.S. PATENT DOCUMENTS 5,495,771 A    3/1996  Sumi
5,524,636 A    6/1996  Sarvazyan et al.
(Continued)

FOREIGN PATENT DOCUMENTS

EP    1 800 603    6/2006
JP    59-190209    10/1984
(Continued)

OTHER PUBLICATIONS

Communication pursuant to Article 94(3) EPC, Application No. 06 746 121.0-1265, issued on Oct. 29, 2012.

*Primary Examiner* — Rochelle Turchen
(74) *Attorney, Agent, or Firm* — Antonelli, Terry, Stout & Kraus, LLP.

(57) ABSTRACT

An image showing the spatial distribution of the hardness of a tissue of an object to be examined from which the influence of the pressure amount is eliminated is displayed.
From ultrasonic tomography data measured by pressing the tissue, a physical quantity relating to the distortion of the tissue at measurement points of the tissue is determined.
An elasticity image of the tissue is created according to the physical quantity.
The physical quantities at the measurement points are indexed by using the physical quantity in a reference region determined in the elasticity image as a reference, and an indexed elasticity image showing the distribution of the index value is created.

1 Claim, 16 Drawing Sheets

(51) Int. Cl.
*A61B 8/14* (2006.01)
*G01S 7/52* (2006.01)

(56) References Cited

U.S. PATENT DOCUMENTS

| | | | |
|---|---|---|---|
| 5,678,565 A * | 10/1997 | Sarvazyan | 600/587 |
| 6,508,768 B1 | 1/2003 | Hall | |
| 7,455,640 B2 * | 11/2008 | Suzuki et al. | 600/437 |
| 2004/0210136 A1 * | 10/2004 | Varghese et al. | 600/443 |
| 2005/0075565 A1 * | 4/2005 | Satoh | 600/437 |
| 2006/0241442 A1 * | 10/2006 | Barthe et al. | 600/439 |

FOREIGN PATENT DOCUMENTS

| | | |
|---|---|---|
| JP | 04-035653 | 2/1992 |
| JP | 05-115480 | 5/1993 |
| JP | 10-146338 | 6/1998 |
| JP | 11-188036 | 7/1999 |
| JP | 2003-88525 | 3/2003 |
| JP | 2004-351062 | 12/2004 |
| JP | 2005-066041 | 3/2005 |
| JP | 2007-105400 | 4/2007 |
| WO | WO 2005/122906 | 12/2005 |
| WO | WO 2006/013916 A1 | 2/2006 |

* cited by examiner

FIG.3
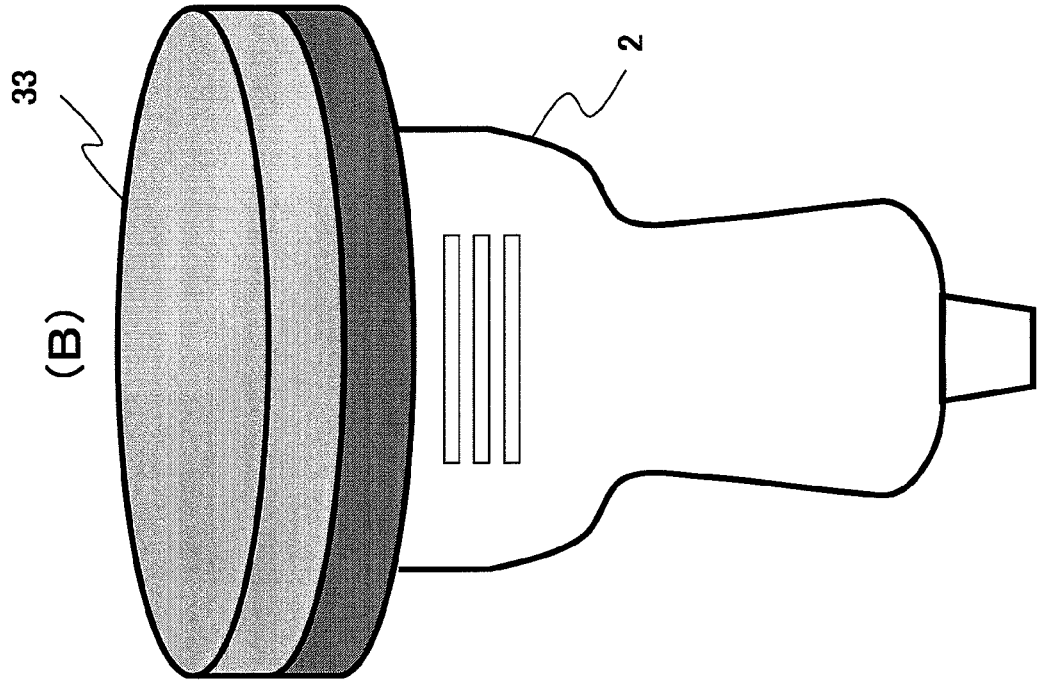
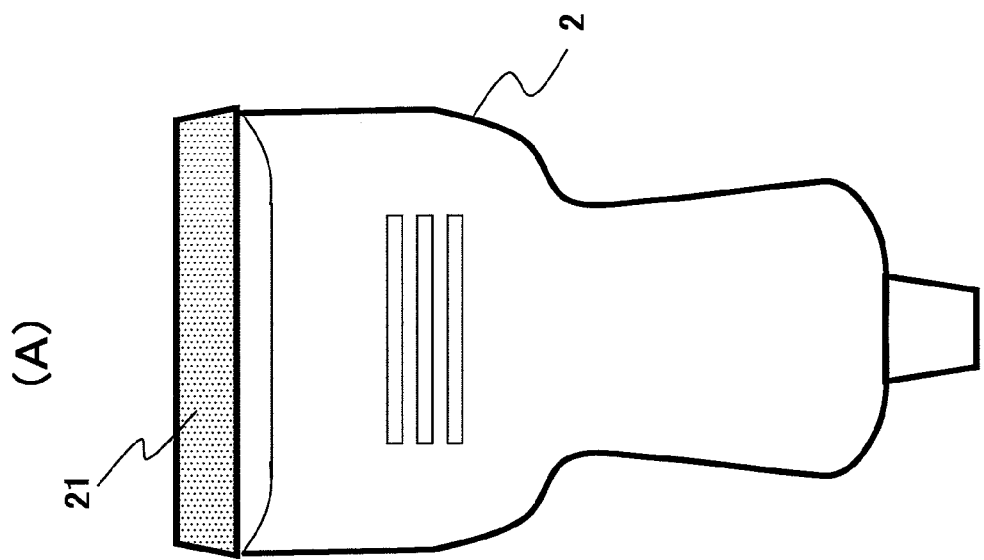

FIG.7
(A)
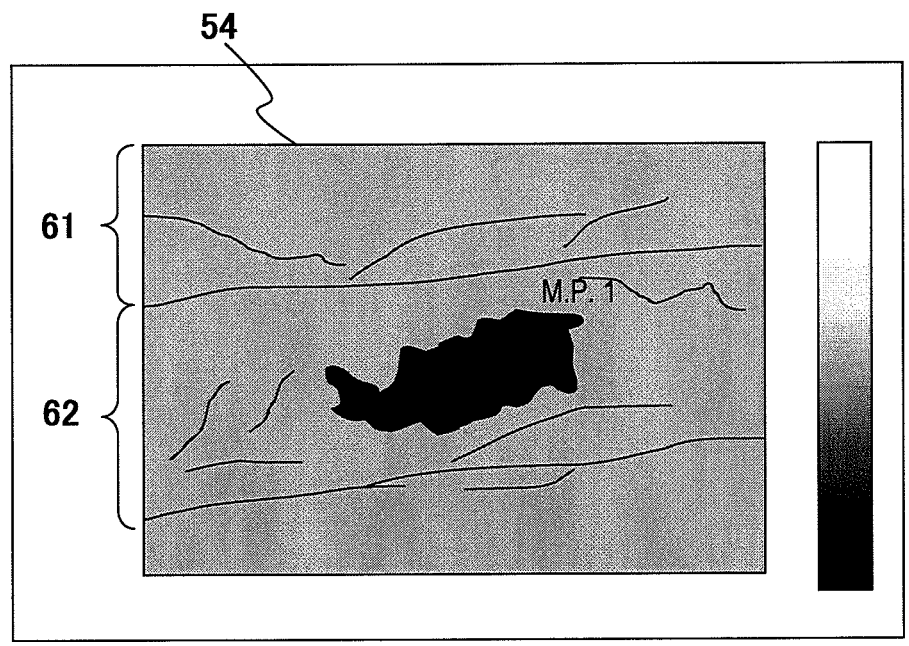
(B)
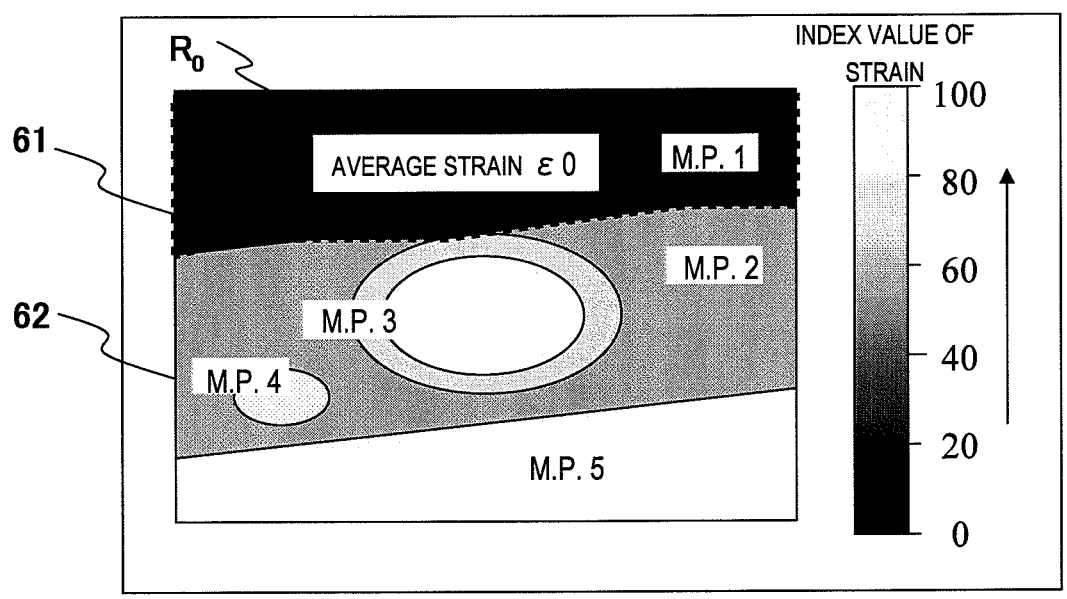
(M.P.:MEASUREMENT POINT)

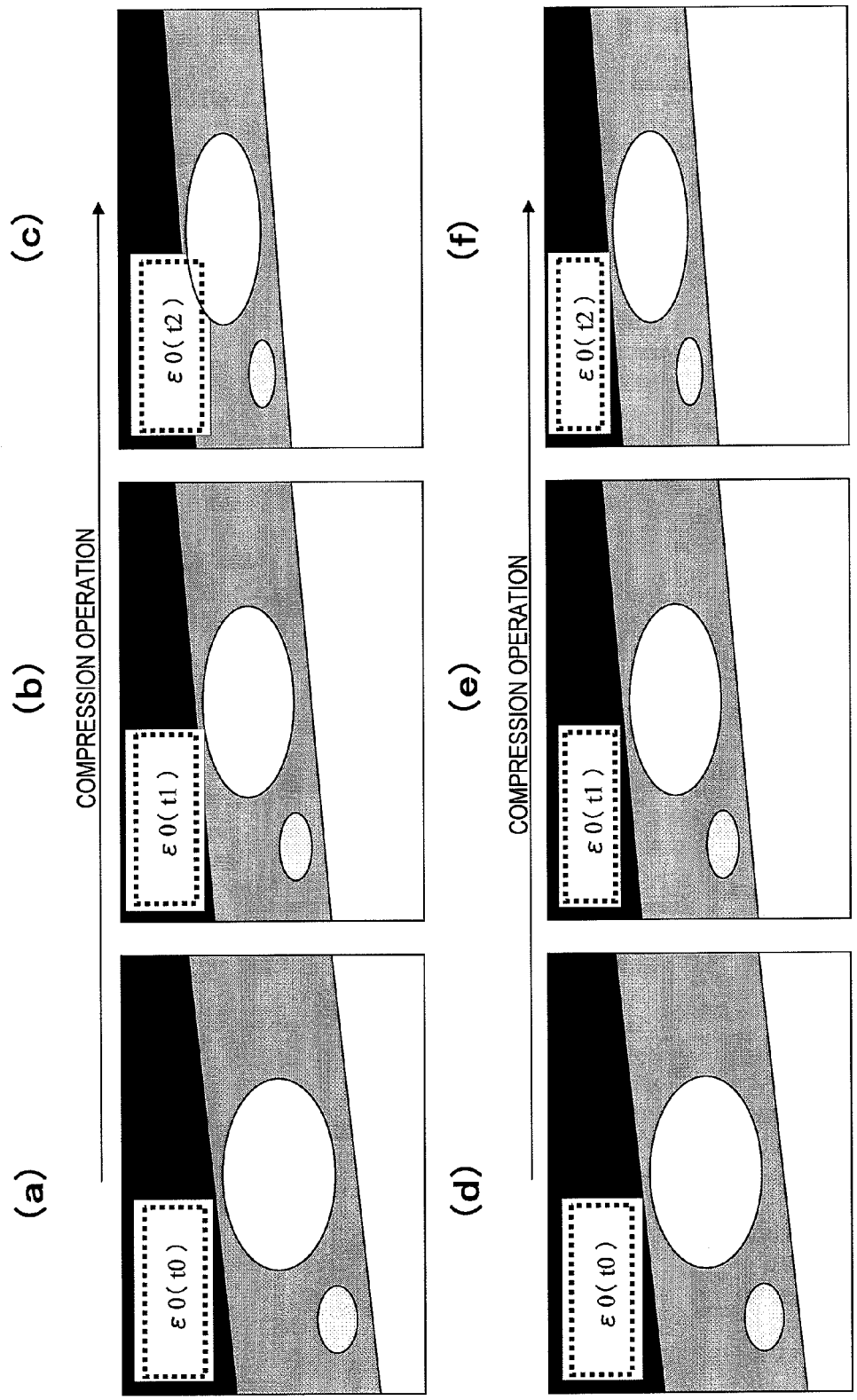

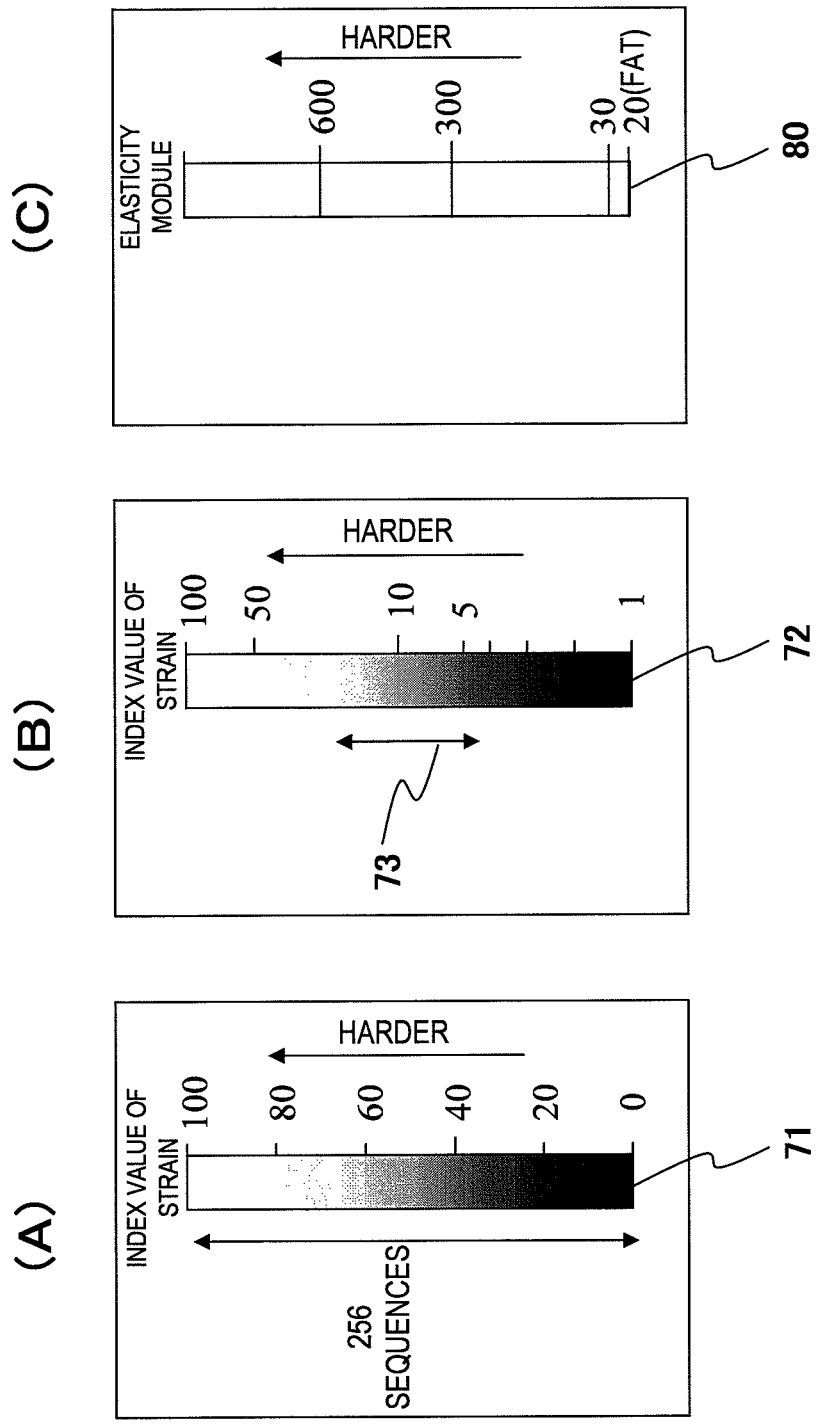

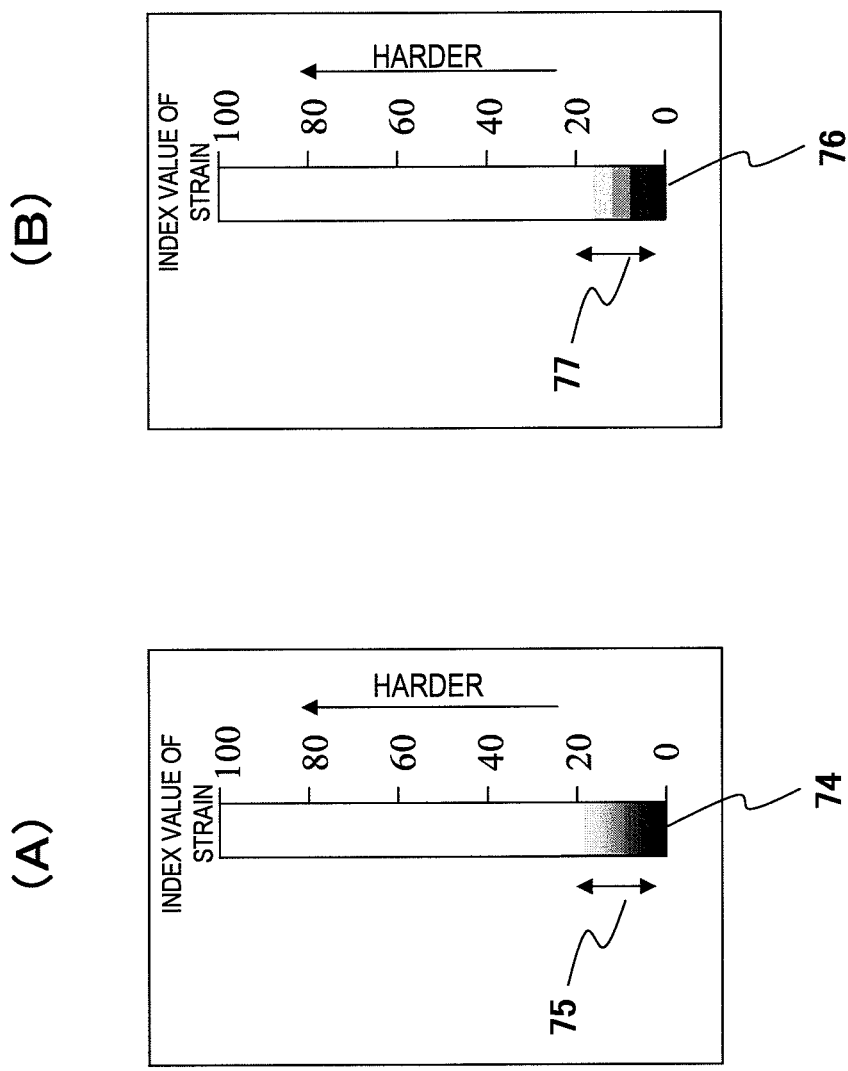

US 9,060,737 B2

ULTRASONIC DIAGNOSTIC APPARATUS AND ULTRASONIC IMAGE DISPLAY METHOD

TECHNICAL FIELD

The present invention relates to an ultrasonic image display method and ultrasonic diagnostic apparatus, in particular to those capable of improving ability for discriminating tissues in diagnosis by providing users the images wherein the physical quantity correlated with strain of tissues of the living body with respect to the compression quantity applied to an object is indexed.

BACKGROUND ART

An ultrasonic diagnostic apparatus is for obtaining displacement of the respective areas of the living body by applying pressure to an object to be examined using manual or mechanical method and imaging information related to the hardness of the tissues based on the obtained displacement, whereby enabling proper discrimination of the diseased tissues such as cancer tumors.

For example, a strain image is one of the hardness information of the tissues and is obtained by acquiring strain of the respective areas in the living body through performing spatial differentiation on a displacement distribution and imparting gradation sequence by hue or brightness in accordance with the degree of strain. However, a strain is a qualitative physical quantity depending on a compression quantity, thus the degree of strain is varied depending on the way of adding pressure. Therefore, the same tissue can be displayed by hue or brightness having greater value of strain just by adding greater pressure, which could lead to a false recognition of discrimination in tissues, depending on the experience or proficiency level of an examiner.

On the other hand, in Patent Document 1, the approach is proposed to obtain hardness property of the tissues that are not correlated with the compression quantity based on the strain image. More specifically, it is suggested to set region of interest ROI-1 and ROI-2 in the diseased tissue and surrounding tissues respectively in the strain image, and to make ratio $\epsilon1/\epsilon2$ of strain $\epsilon1$ and $\epsilon2$ in each ROI as hardness index. By such method, since the relative ratio of the strain between the two regions of interest does not depend on the compression quantity, it is possible to distinguish the difference between strain in the diseased area and its surrounding area almost quantitatively.

Patent Document 1: USPTO WO2006/013916

DISCLOSURE OF THE INVENTION

Problems to be Solved

When the attempt is made to properly distinguish benignity and malignity of the diseased tissue by observing an ultrasonic image of the diseased area such as a cancer tumor, it is effective for proper discrimination to be able to identify the boundary between diseased tissues and normal tissues based on hardness of each area, variation of the hardness of surrounding tissues of the diseased tissues or the hardness of the boundary between the diseased tissues and surrounding tissues.

However, in the technique disclosed in Patent Document 1, while it enables the acquisition of hardness property of the tissues not correlated with pressure quantity in the only regions that are set as the region of interest, attention is not paid to the acquisition of hardness property of the tissues not correlated with pressure quantity in the regions that are not set as the region of interest. Also, since 2-dimensional distribution information of the strain cannot be extracted sufficiently in the ratio between the regions of interest, room for improvement in the technique still remains.

The objective of the present invention is to display as an image the spatial distribution of the hardness of tissues from which influence of compression quantity is eliminated.

In order to achieve the above-mentioned objective, an ultrasonic diagnostic apparatus of the present invention is configured comprising:

an ultrasonic probe;

ultrasonic tomographic data measuring means for adding pressure to the tissues of an object to be examined and measuring the ultrasonic tomographic data of the region;

tomographic image generating means for generating a tomographic image from the ultrasonic tomographic data;

elastic image generating means for obtaining physical quantity correlated with strain of the tissues in a plurality of measurement points of the region based on the ultrasonic tomographic data, and generating an elastic image in the cross-sectional region based on the obtained physical quantity, characterized in further comprising:

means for selecting a reference region in the tomographic image or elastic image; and means for converting physical quantity of the respective measurement points into indexed values on the basis of the physical quantity of the reference region, and generating an indexed elastic image representing the distribution of the index values.

Also, an ultrasonic image display method of the present invention has:

a step for measuring ultrasonic tomographic data by adding pressure to the tissues of an object to be examined;

a step for obtaining physical quantity correlated with strain of the tissues in a plurality of measurement points of a cross-sectional region of the object based on the ultrasonic tomographic data;

a step for generating an elastic image of the cross-sectional region based on the physical quantity;

a step for selecting a reference region in the elastic image;

a step for converting the physical quantity of the respective measurement points into index values based on the physical quantity of the reference region; and a step for generating an indexed elastic image representing distribution of the index values.

In accordance with the ultrasonic diagnostic apparatus and ultrasonic image display method of the above-mentioned present invention, it is possible to display as an image the spatial distribution of hardness of the tissues from which the influence of the compression quantity is eliminated.

BRIEF DESCRIPTION OF THE DIAGRAMS

FIG. 3 is an external view showing an example of an ultrasonic probe.

FIG. 7 is for illustrating an example of an automatic setting method of the reference region related to index values of the present invention.

FIG. 10A illustrates a method for moving a reference region related to the index values of the present invention by making it correlated with the variation of the tissues due to compression.

FIG. 11 is for illustrating an example for imparting gradation sequence to an indexed elastic image related the present invention.

FIG. 12 is for illustrating another example for imparting gradation sequence to an indexed elastic image related to the present invention.

BEST MODE FOR CARRYING OUT THE INVENTION

Hereinafter, the present invention will be described based on the embodiments.

Figure 1:
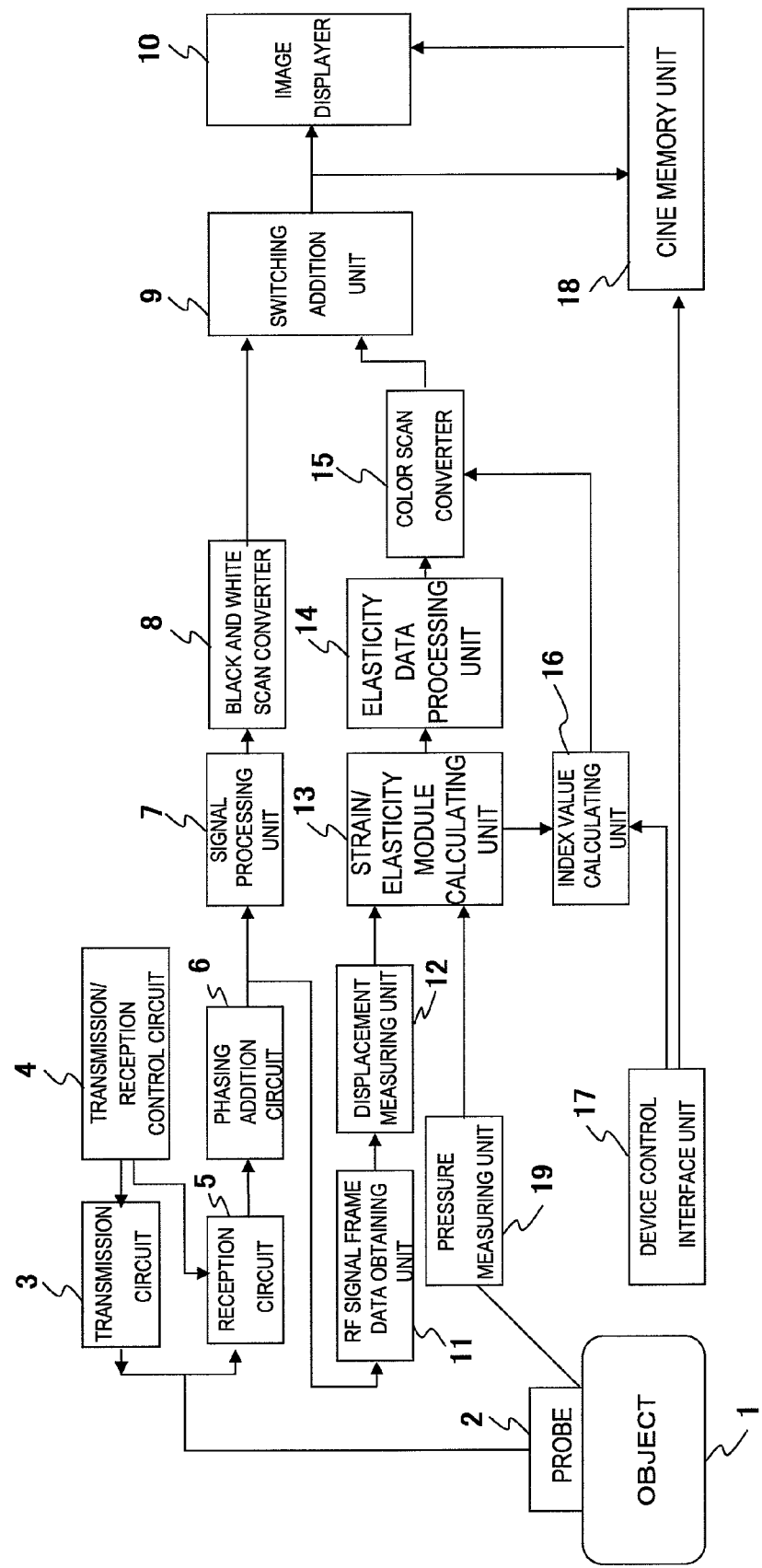
FIG. 1 is a block diagram of an embodiment of the ultrasonic diagnostic apparatus to which the ultrasonic image display method of the present invention is applicable.
Figure 2:
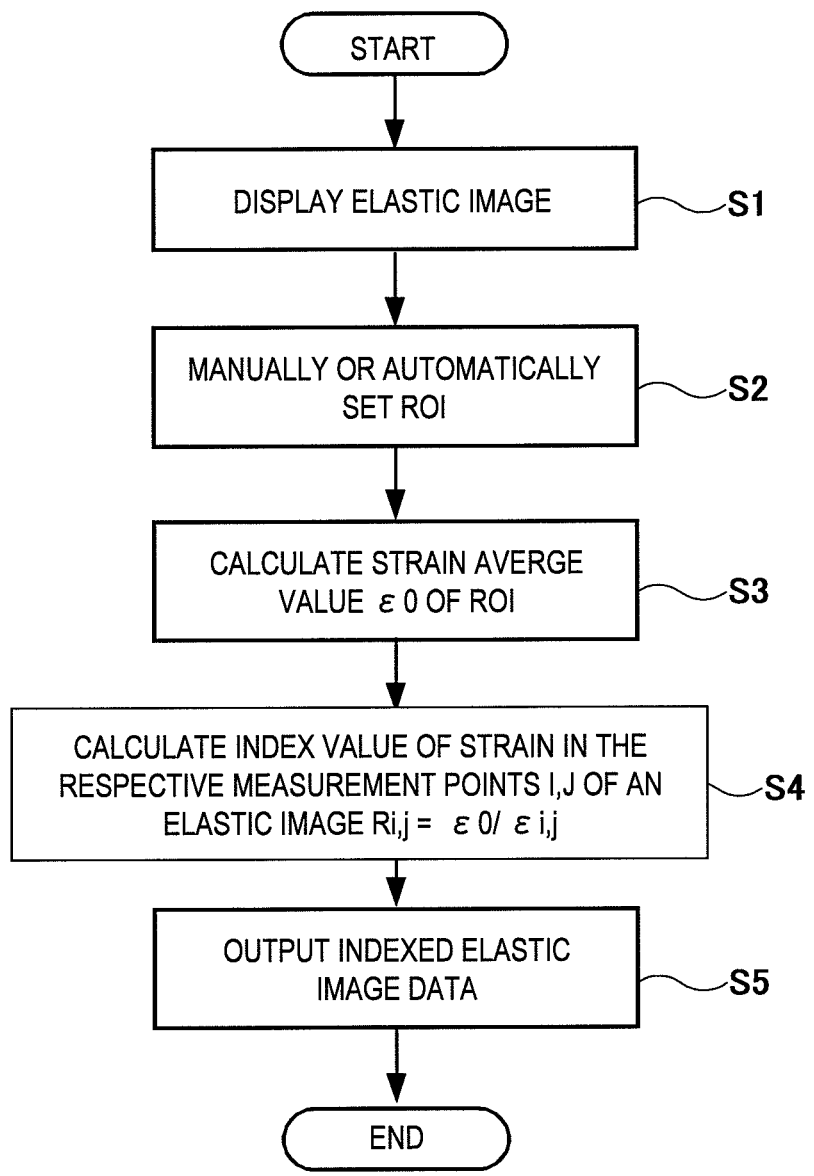
FIG. 2 is a flow chart showing a processing procedure of one embodiment of the ultrasonic image display method related to the present invention.

FIG. 1 shows a block diagram of an ultrasonic diagnostic apparatus of a preferable embodiment for carrying out an ultrasonic image display method related to the present invention. FIG. 2 shows a flow chart of an embodiment of the ultrasonic image display method related to a distinctive feature of the present invention.

Ultrasonic probe 2 is used to apply on object 1 as shown in FIG. 1, and is configured having ultrasonic transmission/reception area 21 in which a plurality of transducers are arranged for transmitting/receiving ultrasonic waves between object 1 as shown in FIG. 3. Probe 2 is driven by ultrasonic pulses provided from transmission circuit 3. Transmission/reception controlling circuit 4 is for forming ultrasonic beams toward a focal point to be set in object 1 by controlling transmission timing of ultrasonic pulses for driving the plurality of transducers of probe 2. Also, transmission/reception controlling circuit 4 electronically scans ultrasonic beams in array direction of the transducers arranged in probe 2.

On the other hand, probe 2 receives reflected echo signals produced from object 1 and outputs them to reception circuit 5. Reception circuit 5 loads the reflected echo signals in accordance with the timing signals inputted from transmission/reception controlling circuit 4 and executes a receiving process such as amplification. The reflected echo signals received and processed by reception circuit 5 are amplified by performing phasing and adding the reflected echo signals received by the plurality of transducers in phasing addition circuit 6. The reflected echo signals performed with phasing addition in phasing addition circuit 6 (hereinafter referred to as ultrasonic tomographic data) are inputted to signal processing unit 7 and performed with signal processing such as gain compensation, log compression, detection and edge enhancement. Radio frequency (RF) signals of the ultrasonic tomographic data generated in the phasing addition circuit may be Q-signals as well that are complexed and demodulated.

The ultrasonic tomographic data processed in signal processing unit 7 is derived to black and white scan converter 8, and is converted into digital signals as well as into 2-dimensional tomographic data corresponding to the scanning area of the ultrasonic beams. Image reconstruction means of the tomogrpahic images is configured by these signal processing unit 7 and black and white scan converter 8. The tomographic image data outputted from black and white scan converter 8 is provided to image displayer 10 via switching addition unit 9, and is displayed as tomographic images.

On the other hand, ultrasonic tomographic data outputted from phasing addition circuit 6 is derived to RF signal frame data obtaining unit 11. RF signal frame data obtaining unit 11 obtains RF signal group corresponding to the scanning area (fault plane) of ultrasonic beams for the portion of a plurality of frames as frame data, and stores them in a device such as a memory. Displacement measuring unit 12 sequentially derives plural pairs of frame data having different acquisition times that are stored in RF signal frame data obtaining unit 11, obtains a displacement vector of a plurality of measurement points in the fault plane based on the pair of derived frame data, and outputs them as displacement frame data to strain/elasticity modulus calculating unit 13.

Strain/elasticity modulus calculating unit 13 obtains strain in the plurality of measurement points in a fault plane based on the inputted displacement frame data, and outputs them as elastic frame data to elastic data processing unit 14. Also, strain/elasticity calculating unit 13 derives pressure measurement data added from pressure measuring unit 19 to the object, obtains stress distribution of the respective areas of the object, obtains stress distribution in the respective regions of the object, acquires elasticity modulus using previously obtained strain frame data and stress distribution, and outputs them as elasticity frame data to elasticity data processing unit 14.

Elasticity data processing unit 14 performs a variety of image processing such as smoothing process in a coordinate plane, contrast optimization and smoothing process in time axis direction among the frames to the strain frame data of strain or elasticity modulus inputted from strain/elasticity modulus calculating unit 13, and outputs them to color scan converter 15.

Color scan converter 15 generates color elastic images by converting elasticity frame data outputted from elasticity data processing unit 14, and displays them on image displayer 10 via switching addition unit 9. More specifically, color scan converter 15 imparts hue codes such as red, green and blue that are sequenced in gradation (for example, 256 gradation sequences) to elastic images, based on the previously set range of the upper limit value and lower limit value of the elasticity (strain or elasticity modulus). For example, the region measured with large strain of the elasticity frame data is converted into red color code, and the region measured with small strain of the elasticity frame data is converted into blue color code. Meantime, a black and white scan converter can be used instead of color scan converter 15. In this case, the region measured with large strain can be displayed with bright luminance, and the region measured with small strain can be displayed with dark luminance.

Also, switching addition unit 9 inputs black and white tomographic image data outputted from black and white scan converter 8 and elastic image data outputted from color scan converter 15, and is formed having a function for displaying one or the other of both images by switching them, a function for displaying on displayer 10 the image wherein one of them is made translucent and superposed over the other image, and a function for displaying both images side-by-side. Also, cine-memory unit 18 stores image data outputted from switching addition unit 9 in memory, calls up past image data according to the command from control interface unit 17 and displays them on image displayer 10. Further, it can transfer the selected image data to a recording media such as MO.

Next, index value calculating unit 16 being an embodiment of the present invention's distinctive feature will be described. Index value calculating unit 16 starts the process according to the control command outputted from control interface unit 17, loads elastic frame data calculated by strain/elasticity modulus calculating unit 13, generates indexed elastic image frame data related to the present invention, and outputs them to color scan converter 15. Color scan converter 15 generates indexed elastic images that are gradation-sequenced based on the indexed elastic image frame data in the same manner as previously mentioned, and displays them on image displayer 10 via switching addition unit 9. The details on index value calculating unit 16 will be described later.

Here, a basic operation of the present embodiment will be described. First, ultrasonic beams are scanned to object 1 while pressure in object 1 is being varied by probe 2, and the reflected echo signals from the scanning area are continuously received. Then a tomographic image is reconstructed by signal processing unit 7 and black and white scan converter 8 based on ultrasonic tomographic data outputted from phasing addition circuit 6, and displayed on image displayer 10.

On the other hand, RF signal frame data obtaining unit 11, while the pressure added to object 1 is being varied, repeatedly obtains frame data by loading ultrasonic tomographic data and identifying them to the frame rate, and stores them in a frame memory incorporated therein in order of time series. Then the plural pairs of frame data are consecutively selected by a pair of frame data having different acquisition time as a unit and outputted to displacement measuring unit 12. Displacement measuring unit 12 performs 1-dimensional or 2-dimensional correlation process on a selected pair of frame data, and generates displacement frame data by measuring the displacement of the respective measurement points in the scanned plane. As for the detection method for the above-mentioned displacement vectors, for example, a block matching method or gradient method disclosed in documents such as JP-A-H5-317313 are known. The block matching method is for dividing an image into, for example, blocks formed by N×N pixels, searching from the previous frame for the most approximated block to the focused block in the present frame and obtaining the displacement of the measurement point based on the searched frame. Also, displacement can be figured out by calculating the autocorrelation in the same region of a pair of RF signal frame data.

Displacement frame data obtained in displacement measuring unit 12 is inputted to strain/elasticity modulus calculating unit 13, and outputted to elasticity data processing unit 14 as elasticity frame data after the strain or elasticity modulus in the respective points are calculated. The strain is calculated, as commonly known, by performing spatial differentiation on displacement distribution. Also, elasticity modulus of the respective measurement points is calculated based on the obtained strain. For obtaining the elastic modulus, the value of pressure measured by pressure measuring unit 19 is loaded, and stress in the respective measurement points are calculated based on the measured pressure value. Pressure measuring unit 19 is configured, for example, having deformable body 33 on the surface of compression plate 31 as shown in FIG. 3(B). Strain/elasticity modulus calculating unit 13 calculates the stress in the measurement points within the body of object 1 on the basis of deformation of reference deformable member 33. In this way, strain/elasticity modulus calculating unit 13 calculates elasticity modulus (for example, Young's modulus Ym) of the respective measurement points on a tomographic image from the stress in the respective measurement points and the strain frame data obtained in strain/elasticity modulus calculating unit 13, and outputs them to elasticity data processing unit 14. Elasticity data processing unit 14 generates elastic image data based on the strain or elasticity modulus, and displays the elasticity images on image displayer 10 via color scan converter 15 and switching addition unit 9.

Next, the detailed configuration related to index value calculating unit 16 that is a distinctive feature of the present embodiment will be described along with its operation dividing into embodiments.

Embodiment 1

Figure 4:
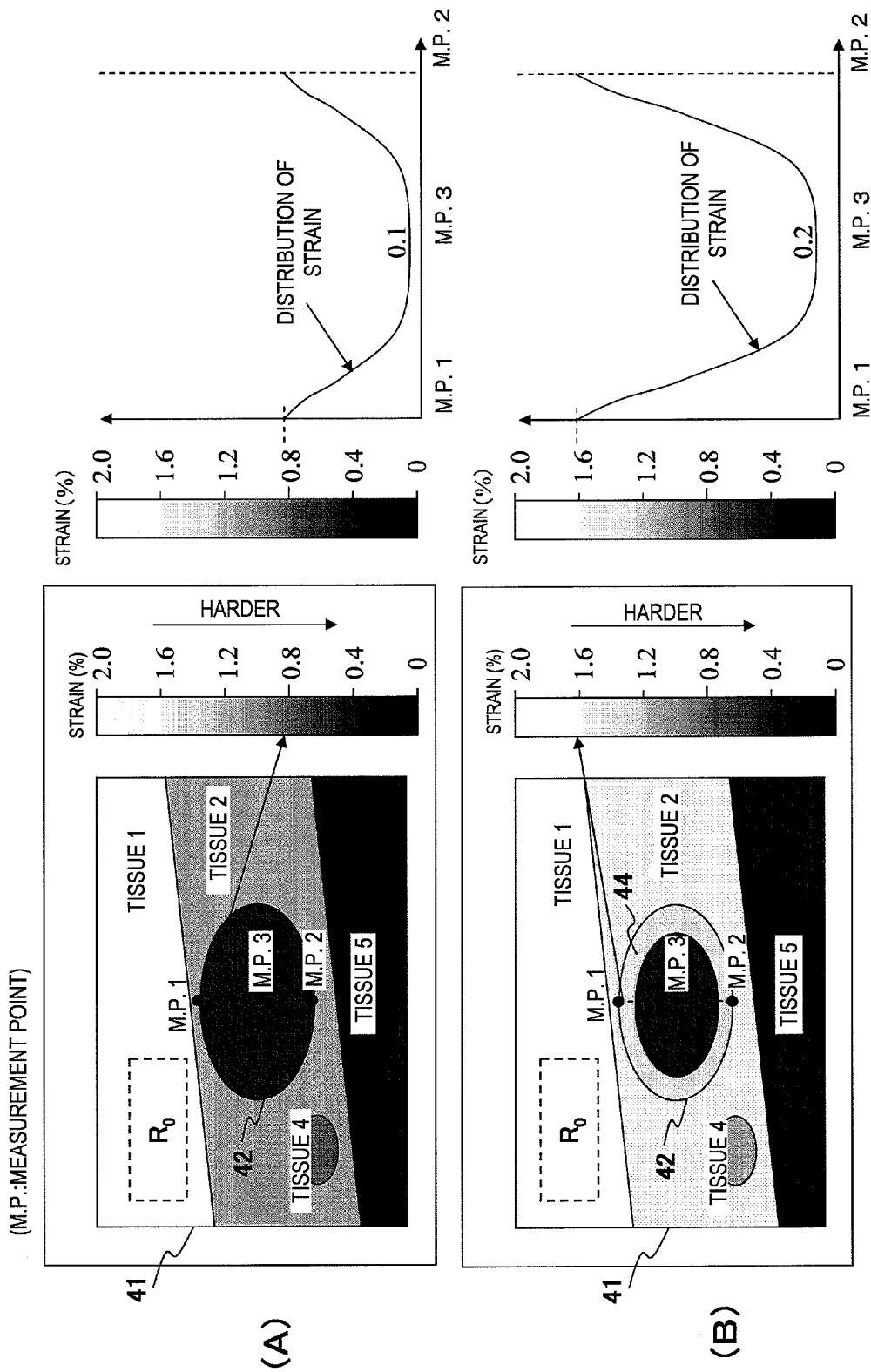
FIG. 4 illustrates the problems of the elastic images of conventional embodiments for explaining the effect of the embodiment related to the present invention.

FIG. 2 is a flow chart of the procedure for generating an indexed elastic image of embodiment 1. The present embodiment is an example for setting reference region $R_0$ to strain image 41 that is one of the elastic images as shown in FIG. 4, and generating indexed elastic image 51 shown in FIG. 5 based on the set reference region and displaying the image.

First, in step S1 of FIG. 2, a command is issued to strain/elasticity modulus calculating unit 13, and strain image 41 is displayed on image displayer 10. Next, coordinate data of reference region $R_0$ being set manually or automatically using a device such as a mouse is loaded via control interface unit 17 (S2). Then the strain image frame data is loaded from strain/elasticity modulus calculating unit 13, and the average value of the strain in the region corresponding to reference region $R_0$ is calculated as reference strain $\epsilon_0$ (S3). Next, index value $R_{i,j}$ which is the correlation rate between strain $\epsilon_{i,j}$ in each strain measurement point (i,j) and reference strain $\epsilon_0$ is obtained using the following formula (S). The indexed elastic image data formed by the obtained $R_{i,j}$ is outputted to color scan converter 15 (S5). By doing so, the indexed elastic image wherein the strain of the respective measurement points is normalized by reference strain $\epsilon_0$ is displayed on image displayer 10.

$$R_{i,j} = \epsilon_0 / \epsilon_{i,j} \tag{1}$$

Any index reflecting the difference between $\epsilon_0$ and $\epsilon_{i,j}$ may be used for index value $R_{i,j}$ without being limited to the rate. For example, $$R_{i,j} = \log(\epsilon_0) - \log(\epsilon_{i,j})$$

may be used. Or, when $$R_{i,j} = (\epsilon_0 - \epsilon_{i,j})/(\epsilon_0 + \epsilon_{i,j}), \text{ or}$$

$$R_{i,j} = (\epsilon_0 - \epsilon_{i,j})/\epsilon_0,$$

it becomes $\epsilon_{i,j} \sim 0$ in the measurement point of the hard region and $\epsilon_{i,j} \sim \epsilon_0$ in the measurement point in the soft region, thus the index can be made to be normalized to take a value between 0 and 1 in a way as:

Hard measurement point: $R_{i,j} \Rightarrow 1$,
Soft measurement point: $R_{i,j} \Rightarrow 0$.

Figure 5:
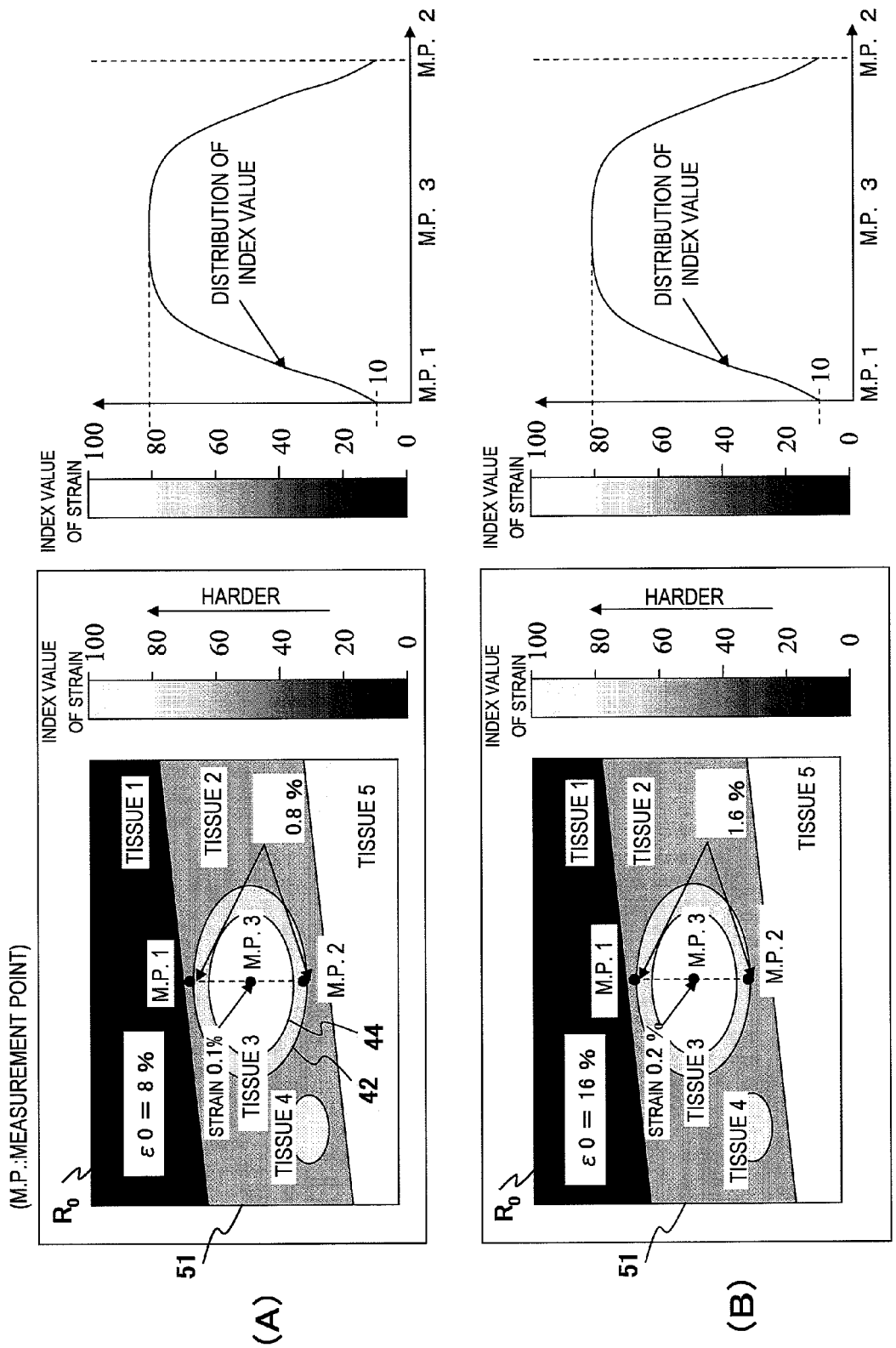
FIG. 5 shows an indexed elastic image of an embodiment related to the present invention.

Advantageous effect of the present embodiment will be concretely described referring to FIG. 4 and FIG. 5. First, in the case of freely pressing the tissues of the living body and measuring the strain thereof, the degree of the strain depends on the compression quantity at that point. Suppose, for example, in the compression quantity at one point the strain is measured as 0.8% in measurement point 1 and measurement point 2, and as 0.1% in measurement point 3 in the living body as shown in FIG. 4(A). On the other hand, the compression quantity at the different point could be measured, as shown in FIG. 4(B), as 1.6% in measurement point 1 and measurement point 2, and as 0.2% in measurement point 3. When such strain image is performed with gradation sequence based on the degree of the strain (%), as shown in FIG. 4(B), the image pattern can be obtained having a bordering around tumor section 42 of the area of interest when the compression quantity is measured as 1.6% in the measurement points 1 and 2. However, when the compression quantity is measured as 0.8% in measurement points 1 and 2 as shown in FIG. 4(A), since the range of the gradation sequence level changes to the range having low sensitivity it is difficult to display a clear image pattern of the bordering around tumor section 42 in the area of interest. In other words, even when the tissues are the same in the image diagnosis based on the strain image, since the intensity of the hue or brightness and the pattern of the diseased area varies according to the compression quantity at the time, it becomes difficult to properly identify the boundary of the diseased area. In addition, the diagrams shown on the right-hand side of FIGS. 4 (A) and (B) are showing the each of the strain distribution on the analysis line connecting measurement points 1 and 2.

On the other hand, in accordance with the present embodiment, as shown in FIGS. 5(A) and (B), since indexed elastic image 51 is generated by setting reference region $R_0$, setting the average value of the strain in the set region as reference strain $\epsilon_0$, and imparting gradation sequence based on index value $R_{i,j}$ of the strain wherein strain of the respective measurement point$_{i,j}$ is normalized, it is possible to obtain the information of the distinctive hardness of tissues without depending on the compression quantity. As a result, as is apparent from the comparison of FIG. 5(A) and FIG. 5(B), indexed elastic image 51 wherein the gradation sequence distribution such as luminance distribution does not vary can be obtained, even when reference strain $\epsilon_0$ of reference region $R_0$ set in the same tissue 1 are different such as 8% or 16% due to the difference of the compression quantity. Therefore, image pattern of the bordering around tumor section 42 in the area of interest can be identified with high sensitivity. In particular, difference of hardness between surrounding tissue 2 of tumor region 42 and boundary tissue 44 can be identified. The diagrams shown on the right hand of FIGS. 5(A) and (B) show the distribution of index value on the analysis line connecting measurement points 1 and 2.

For example, fat is the softest tissues in the measuring cross-sectional surface in a breast cancer screening test. When reference region $R_0$ is set in this region, since the regions besides the reference region are harder than the fat, correlation ratio that is index value $R_{i,j}$ of the strain has a value which is more than 1, and the harder the tissues are the greater the value of the correlation ratio is measured. Or, reference region $R_0$ may be set in a greater pectoral muscle. Since the greater pectoral muscles are fixed by being supported by rib bones, the reference strain can be detected with high sensitivity. Also, while thickness of fat varies between individuals and it is difficult to secure the sufficient size of a region as the reference region, greater pectoral muscles has few variations between individuals and can surely be used as the measurement area.

As for an abdominal area, an indexed elastic image of, for example, a liver may be generated by setting the reference region in the liver and obtaining ratio $R_{i,j}$ between the strain in the respective measurement points (i,j) based on formula (1).

Also, in the case of imaging a prostate gland region, fatty tissue in the capsule portion of the prostate gland may be set as the reference region.

While an example for generating an indexed elastic image using an elastic image is described in the present embodiment, the present invention is not limited to this, and the same effect as the present embodiment can be obtained by generating an indexed elastic image using property data of the tissue such as elasticity or viscosity that are information related to the hardness property of the tissue.

Also, while index value $R_{i,j}$ is obtained by setting the average value of the strain in reference region $R_0$ as reference strain $\epsilon_0$, the present invention is not limited to this and strain $\epsilon_{i,j}$ of the respective measurement points can be normalized by setting values such as a median of the strain in reference region $R_0$ or the strain values which are counted most frequently in a process such as histogram process as reference strain $\epsilon_0$.

Also, instead of setting reference region $R_0$ as a certain range of region including a plurality of measurement points, a value of the strain of one measurement point may be set as reference strain $\epsilon_0$ as the reference region.

As mentioned above, indexed elastic images of the present invention are displayed as images of the index value wherein the physical quantity correlated with the strain in a plurality of measurement points of the cross-section region is normalized, on the basis of the physical quantity correlated with the strain of the set reference region. The index value is a relative value of the respective regions having received the same compression quantity, thus the index value hardly varies even when the compression quantity is varied. Therefore, indexed elastic images of the present invention can display the hardness variation from the diseased tissues to the surrounding tissues or the difference of hardness in the boundary region semi-quantitatively on the basis of the hardness in the reference region by eliminating the influence of the compression quantity. As a result, benignity or malignity of diseased tissue can be identified subjectively, universally and appropriately.

Embodiment 2

Figure 6:
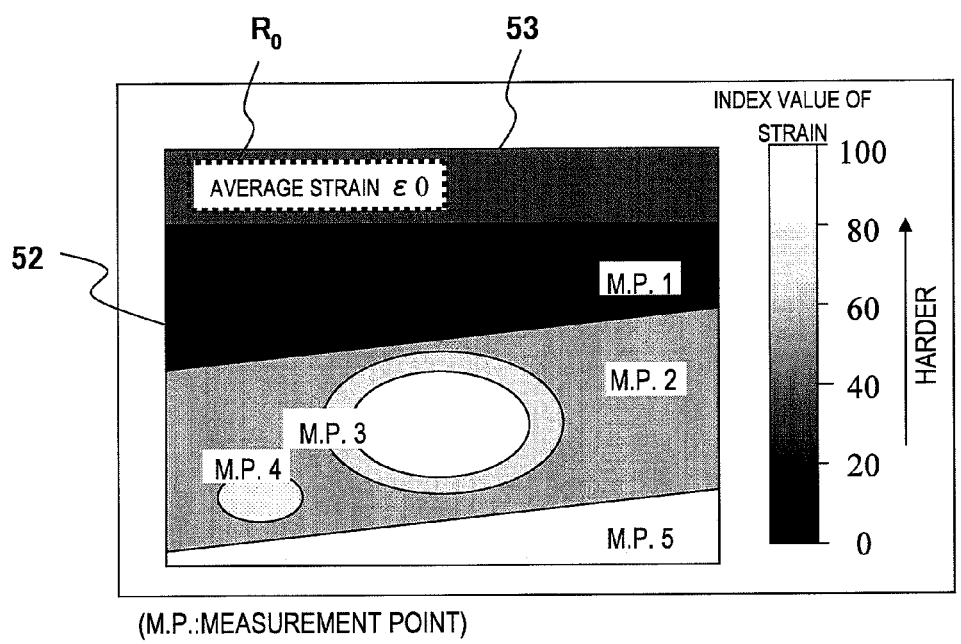
FIG. 6 shows an indexed elastic image of another embodiment related to the present invention.

In embodiment 1, an example for setting reference region $R_0$ being the reference region for indexing in the living body is described. However, the present invention is not limited to this, and when ultrasonic tomographic data is obtained using probe 2 having reference deformable member 33 which is an elastic member shown in FIG. 3(B), image 53 of reference deformable member 33 is displayed in the tissue region located in the nearest to probe 2 on the strain image as shown in FIG. 6. In the same manner as embodiment 1, indexed elastic image 52 can be generated and displayed by setting reference region $R_0$ in this image region of reference deformable member 33.

In particular, it is possible to estimate an approximate elasticity module of the tissues in the respective measurement points by measuring elasticity module of reference deformable member 33 in advance. More specifically, by setting elasticity modulus of reference deformable member 33 as Eref(kPa), approximate elastic modulus $E_{i,j}$ of the respective points can be obtained. And more meticulous image information on hardness can be obtained by imaging the above-obtained elastic modulus in the respective measurement points.

$$E_{i,j} = \text{Eref} \times R_{i,j} (\text{kPa}) \quad (2)$$

While an example for using an extracorporeal reference deformable member is described in the explanation above, the present invention is not limited to this, and the reference deformable member can be placed inside the body of the object. For example, in the case of imaging a prostate gland, a catheter to be inserted from a groin is used as the reference deformable member. This catheter is not hollow, and filled with a material such as rubber. Outer diameter of the catheter is 1~2 mm.

In the case of imaging a prostate gland, the imaging is carried out using a probe made exclusively for imaging a prostate gland. There is a blood vessel in the vicinity of the prostate gland from which the catheter is inserted, and a cross-sectional surface of the catheter is displayed on the image to be obtained. This catheter region is set as the reference deformable member.

Also, by attaching an elastic balloon at the end of a hollow catheter, the balloon to be inserted in the body may be used as the reference deformable member. This balloon is hallow inside, and is expandable by inserting liquid substance such as liquid rubber or jelly therein. Outer periphery upon expansion is 0.5~5 mm, and it can be arbitrarily set by adjusting the amount of liquid to insert.

Embodiment 3

While an example is described in embodiment 1 for setting reference region $R_0$ by inputting from control interface 17, reference region $R_0$ can be also set automatically as described below. For example, by detecting the softest region in an image such as an elastic image, and reference region $R_0$ may be set thereto.

Also, for example, FIG. 7(A) shows B-mode tomographic image 54 of a mammary gland wherein fatty tissues that are positioned nearest to probe 2 appear thereon, which are also the softest tissues in the measurement region. Here, since it is possible to detect the boundary between fat 61 and mammary gland 62 also on B-mode image 54, the region from the vicinity of the body surface to the boundary of the mammary gland can be extracted and automatically set as reference region $R_0$.

In this case, as shown in FIG. 7(B), indexed elastic image 55 having reference region $R_0$ that is the whole tissue 1 of fatty tissue 61 can be obtained.

Figure 8:
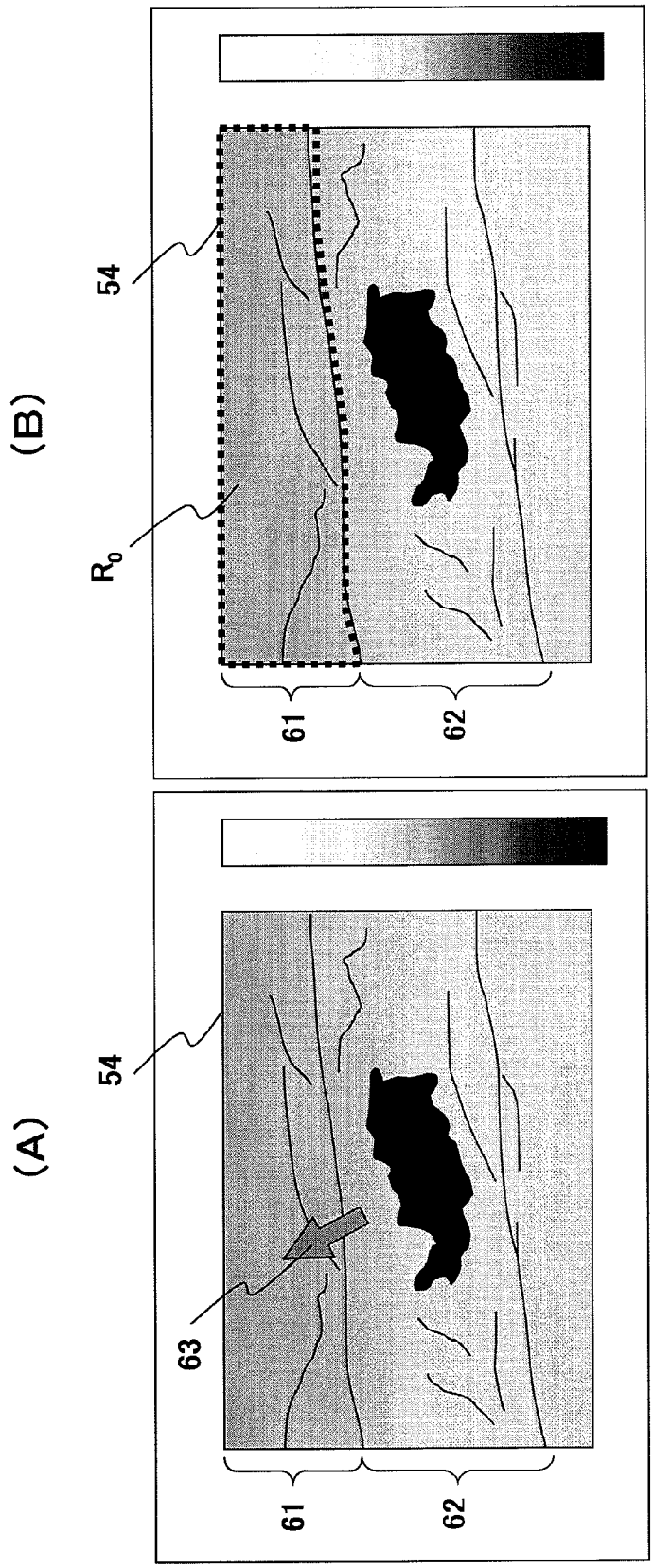
FIG. 8 is for illustrating another example of an automatic setting method of the reference region related to an index value of the present invention.

Also, for example, it is possible to automatically set reference region $R_0$ by moving cursor 63 using an input device such as a mouse to a desired reference region on the display image, clicking the device for specifying the region as shown in FIG. 8(A) and identifying the same tissue region including the specified region as shown in FIG. 8(B) based on elasticity information such as a strain value, brightness information or pattern information of a B-mode image.

In this way, arbitrary properties as to the setting of reference region $R_0$ are eliminated by the automatic setting of reference region $R_0$ whereby enabling the objective diagnosis of hardness using indexed elasticity images.

Figure 9:
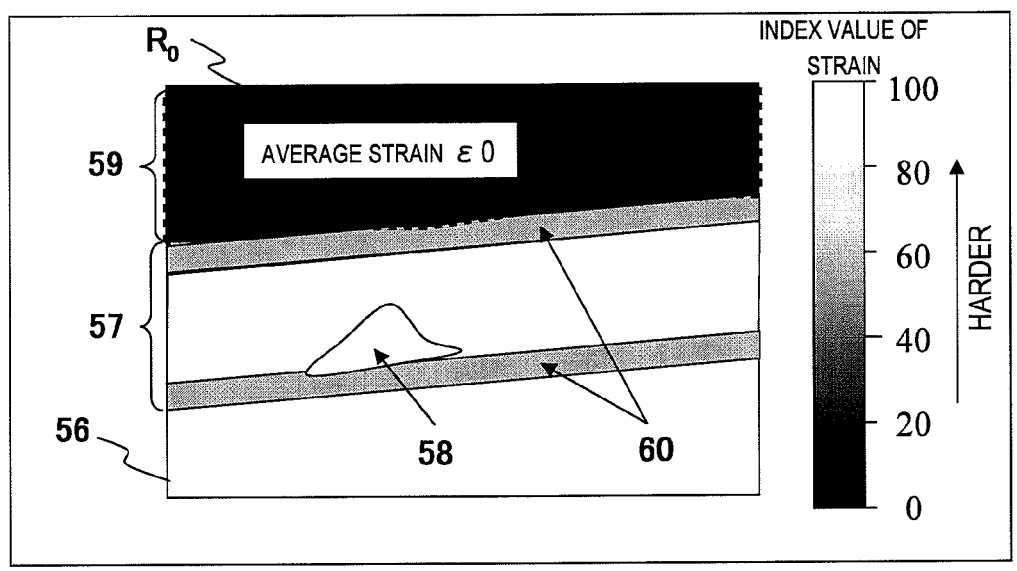
FIG. 9 illustrates an indexed elastic image of another embodiment related to the present invention.

While an example of a mammary gland is described in the explanation above, the present invention is not limited to this and can also be applied to the elasticity assessment of a region such as plaque 58 in carotid artery 57 as shown in indexed elasticity image 56 of FIG. 9. In this case, for example, the region of muscle 59 can be set as reference region $R_0$ and the index value of the strain with respect to blood vessel wall 60 or plaque 58 can be imaged and diagnosed.

Embodiment 4

Figure 10B:
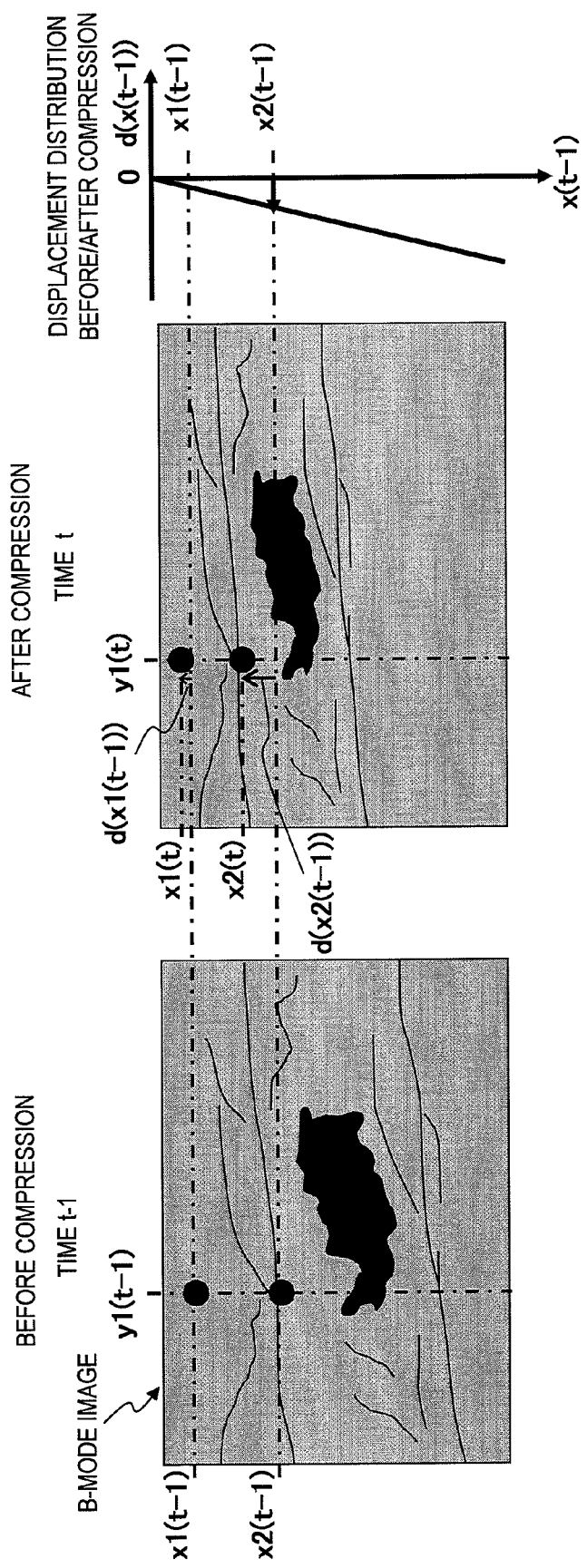
FIG. 10B illustrates a concrete embodiment of the follow-up process of the points for forming reference region $R_0$ related to the index value of the present invention.

There are occasions, when the tissues are moved during the compression process, that reference region $R_0$ being set in the respective above-described embodiments wander from the region set in the same tissues. That is, when reference region $R_0$ is consistently fixed and set as a constant coordinate region as shown in FIG. 10 A(a)~(c), other tissues enter into the region of reference region $R_0$ while being pressed.

In this case, as shown in FIG. 10 A(d)~(f), it is desirable to variably set reference region $R_0$ consistently followed by the same tissue region. By doing so, other tissues will not enter into reference region $R_0$ while being pressed thus the strain value measured in the same tissues can be consistently set as reference strain value $\epsilon_0$ and accurate index values can be acquired without disturbance, whereby improving dependability for diagnosis.

Concrete embodiment for the above-mentioned follow-up process of reference region $R_0$ will be described below. The process by which displacement distribution (displacement frame data) is obtained in displacement measuring unit 12 of FIG. 1 will be concretely illustrated using FIG. 10(B).

For example, coordinate system wherein y-coordinate is set on the B-mode image and x-coordinate is set in depth direction is provided, and the attention is paid to these two measurement points (x1,y1) and (x2,y1) being in the direction along line y1. As shown in the diagram, the target tissues shall be set to have been compressed during time variance from time t−1 (past) to time t (present).

The tissue which was at coordinate (x1(t−1),y1(t−1)) in time t−1 is moved to coordinate (x1(t), y1(t)) at time "t", and in the same manner, the tissue which was at coordinate (x2(t−1),y1(t−1)) in time t−1 is moved to coordinate (x2(t),y1(t)) at time "t".

At this time, in displacement measuring unit 12, displacement d(x,y) at all measurement points (x,y) is calculated, for example, displacement distribution d(x(t−1) along line y1 from the above-mentioned time t−1 to "t" is obtained as shown in the diagram, and x-coordinate x1(t),x2(t) after the above-mentioned movement in the present time "t" can be obtained respectively as:

$$X1(t) = x1(t-1) + d(x1(t-1))$$

$$X2(t) = x2(t-1) + d(x2(t-1)).$$

Coordinate y1(t),y2(t) after movement in y-coordinate direction can be obtained in the same manner.

Figure 10C:
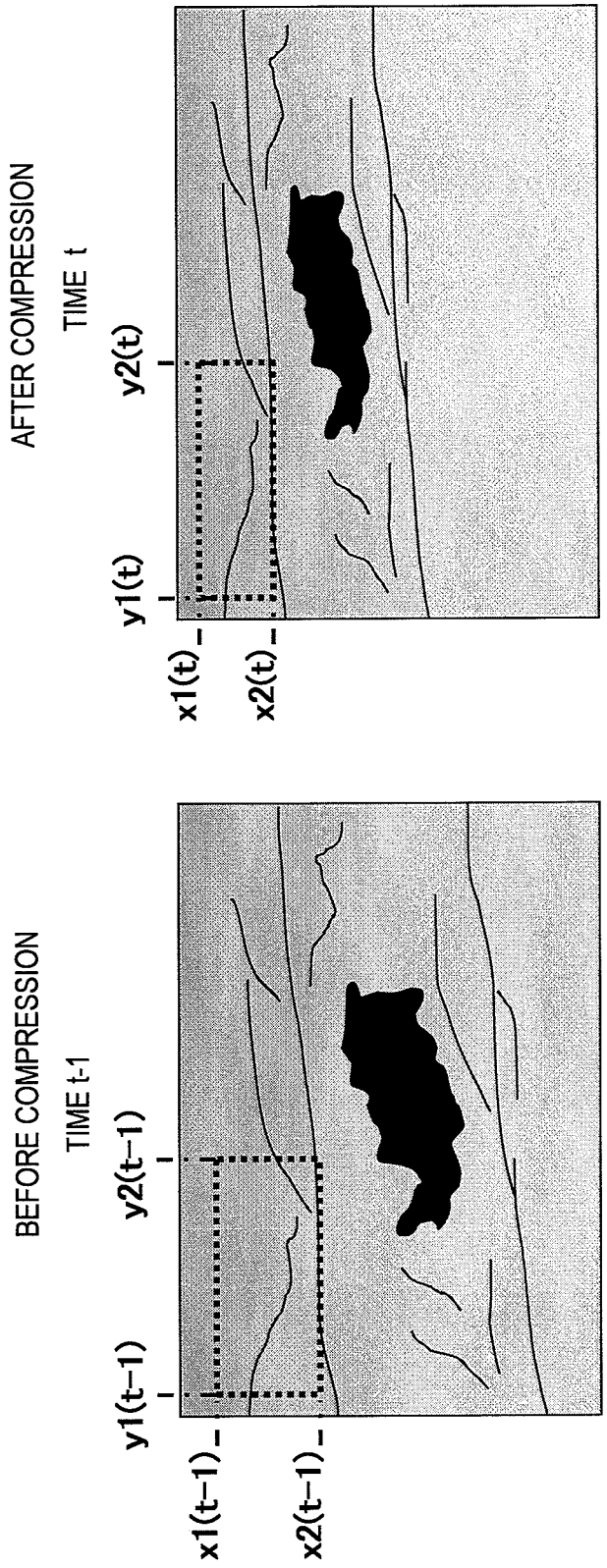
FIG. 10C illustrates a concrete embodiment of the follow-up process of reference region $R_0$ related to an index value of the present invention.

Based on the above-mentioned method, for example as shown in FIG. 10(C), when a rectangle reference region $R_0$ formed by four points (x1(t−1),y1(t−1)), (x2(t−1),y1(t−1)), (x1 (t−1),y2(t−1)),(x2(t−1),y2(t−1)) is set at time t−1, it is possible to determine where the tissues in the above-mentioned 4-points moved to, thus the same tissue region is to be specified as the tissues within $R_0$.

It is possible in this method to perform the above-mentioned process in real time, and to make the same tissue region to be performed with tracking and follow-up as reference region $R_0$ as shown in FIG. 10A.

While a follow-up process using displacement information in the coordinate of four-points placed at the corners for specifying reference region $R_0$ is described in the explanation above, without being limited to this method, the follow-up process may be performed using displacement information in a coordinate placed along the line representing the boundary of reference region $R_0$ whereby making the process highly accurate by being based on greater variation of information.

Also, the follow-up process may be performed using displacement information in the coordinate within reference region $R_0$ to obtain yet higher accuracy.

Embodiment 5

While correspondence between an index value and a gradation sequence level upon imparting gradation sequence on an indexed elastic image based on the index value in the respective measurement points is not particularly mentioned in the above-described respective embodiments, a variety of functions such as proportional function, logarithmic function and setting function in which the resolution in the vicinity of the threshold value for determining benignity/malignity of the tissues is raised higher can be applied to the index function for defining the relationship between the index value and the gradation sequence level.

In concrete terms, as shown in bar display 71 of FIG. 11(A), gradation sequence function is set as a proportional function, and the index value and a gradation sequence map of, for example, 8 bits having 256 sequences expressed by hue and brightness can be allocated to a linear relationship.

Also, as shown in bar display 72 of FIG. 11(B), an index function can be defined by a logarithmic function. Particularly in range 73 within which hue and brightness sensitively vary, it is also possible to define the specified function wherein threshold value Rth is set. For example, in the case that threshold value Rth of the index value for effectively identifying benignity/malignity is being obtained, it is possible to identify benignity/malignity on the image with high accuracy by defining gradation sequence function wherein the hue and brightness sensitively vary.

Also, as shown in bar display 80 of FIG. 11(C), a specified region as an index of the elasticity module may be displayed. For example, a fat region being a normal region that is 20 kPa is displayed as an index. Other regions are also converted into elasticity modulus and displayed. Thus benignity/malignity can be identified with respect to the normal region on an image with high sensitivity.

Furthermore, as shown in range 75 of bar display 74 in FIG. 12(A), it is possible to perform mapping by preparing and using a gradation sequence function of a special gradation sequence map wherein the hue or brightness drastically vary between cases in which index value of strain is greater or lesser than threshold value Rth. Also, as shown in FIG. 12(B), the hue or brightness of the gradation sequence map can be set to vary stepwise and discontinuously in range 77 where the index value of bar display 76 is small.

Figure 13:
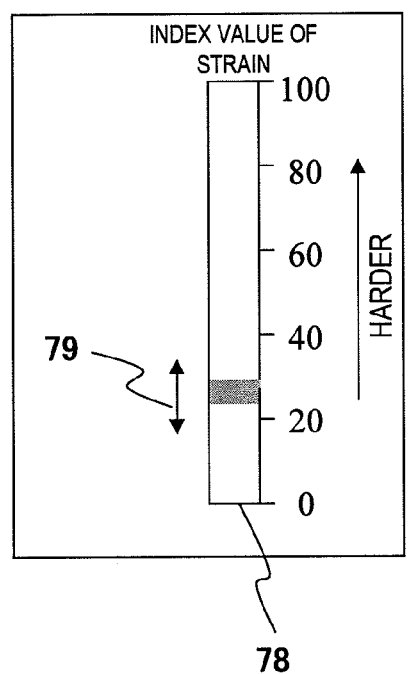
FIG. 13 is for illustrating yet another example for imparting gradation sequence to an indexed elastic image related to the present invention.

Also, as shown in FIG. 13, by setting a definite colored range 79 in the vicinity of, for example, threshold Rth in bar display 78 and changing the threshold value Rth by an examiner moving the colored range 79 up and down using a pointing device, it is possible to easily analyze which range the index value of the region of interest falls into. At the same time, it can be set so that the examiner carries out a process such as moving threshold value Rth up and down in real time and coloring only the region surpassing the threshold value Rth.

As a result, by setting a specific region of interest in a diseased area for constructing an indexed elastic image, obtaining an index value of the region of interest and freely moving the position of threshold value Rth of the gradation sequence map without displaying the obtained index value, it is possible to grasp the index value of the hardness of tissues in the region of interest easily and accurately.

Embodiment 6

Figure 14:
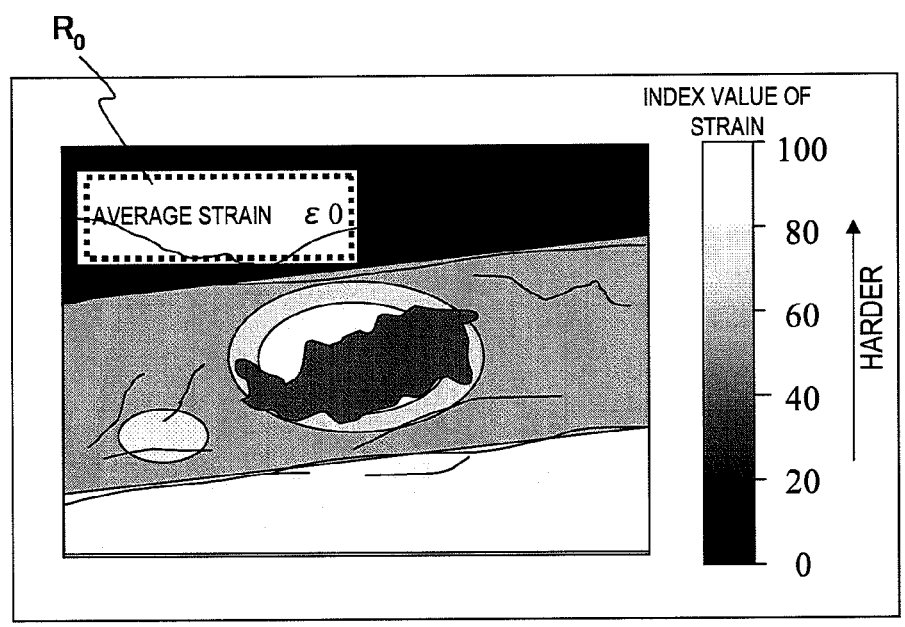
FIG. 14 is for illustrating an example for displaying an indexed elastic image by superimposing a B-mode image on it.

The indexed elastic image formed in the above-mentioned respective embodiments can be displayed independently or aligning with an elastic image such as B-mode image or strain image. Further, for example, it may be set as shown in FIG. 14 so that an indexed elastic image will be displayed as a colored translucent image being superimposed on a black and white B-mode image.

Also, in the case, for example, that a B-mode image and an indexed elastic image are displayed in two screens independently, the size or position of reference region $R_0$ of the indexed elastic image can be variably set having the B-mode as a guide. Also, without being limited to a B-mode image, reference region $R_0$ may be set having an image displayed being paired with an indexed elastic image as a guide.

Embodiment 7

Figure 15:
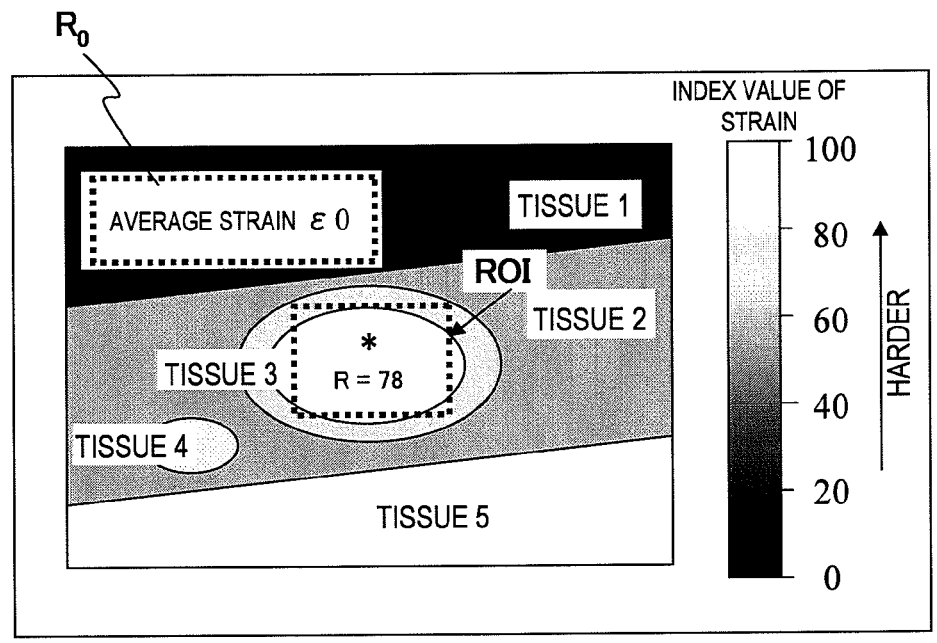
FIG. 15 is for illustrating an embodiment for setting an ROI in an indexed elastic image related to the present invention, and numerically displaying an average value of the index value with respect to the hardness of the ROI.

Furthermore, the present invention is able to perform an analysis of the hardness of reference region $R_0$ and the tissues by setting ROI in the displayed indexed elastic image. For example, as shown in FIG. 15, by setting ROI on an indexed elasticity image and obtaining a value such as the average value of the strain in the ROI, the obtained value can be corresponded, for example, to the vicinity of the ROI and displayed. Also, a plurality of such ROI can be set for the above-mentioned method.

Embodiment 8

While display of indexed elastic images by generating them in real time with B-mode image or strain image is described on the above-mentioned respective embodiments, the present invention is not limited to this, and indexed elastic images may be generated and displayed by selecting settings off-line after freezing and using elastic frame data stored in a cine memory.

Embodiment 9

While it is estimated that the biomedical tissues in object 1 are compressed evenly by probe 2 in the above-mentioned respective embodiments, the tissues are compressed unevenly in cases such as probe 2 being tilted upon compression with respect to the body surface of object 1. In particular, the compression becomes uneven in a direction vertical to transmission/reception direction (sound-ray direction) (hereinafter referred to as lateral direction). As a result, there is a possibility that the index value becomes inaccurate due to the unevenness of the strain of the reference region in lateral direction. Given this factor, the present embodiment obtains the index value with high accuracy even when the strain of the reference region is uneven, by eliminating the influence thereof. To achieve the above-mentioned purpose, the whole image region is segmentalized in lateral direction, so that the compression can be ascribed evenly in the respective segmentalized regions. Then the index value is calculated with respect to every segmentalized region.

Figure 16:
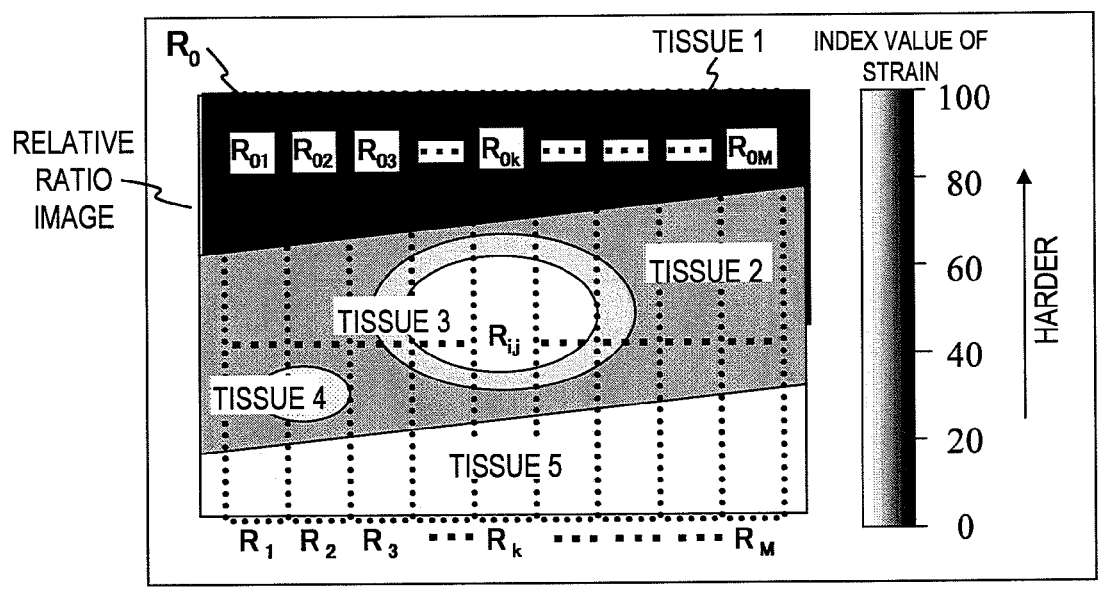
FIG. 16 illustrates an embodiment for generating an indexed elastic image as a whole by segmenting the elastic image in lateral direction and indexing with respect to every segmented image.

The present embodiment will be described concretely referring to FIG. 16. FIG. 16 is an indexed elastic image displayed on image displayer 10 and is an example showing an indexed elastic image including the reference regions and the other regions. By segmentalizing this indexed elastic image into strips in lateral direction, for example, into M-numbers, a plurality of elongated segmented regions $R_1$, $R_2, \ldots, R_k, \ldots R_M$ that are parallel to sound-ray direction are obtained. The reference region in the respective segmented regions is obtained as segmented reference regions $R_{01}$, $R_{02}, \ldots, R_{0k}, \ldots R_{0M}$. The width of the respective segmented reference region in lateral direction can be set as, for example, at several mm. Then, the index value of the strain in the respective measurement points are obtained using reference strain $\epsilon_{01}, \epsilon_{02}, \ldots, \epsilon_{0k}, \ldots \epsilon_{0M}$ of the segmented reference region in the segmented region of the measurement point. In other words, for example, as shown in FIG. 16, strain $\epsilon_{i,j}$ measured in measurement point (i,j) is assumed to be given via segmented reference region $R_{0k}$ within the segmented region. In view of this, index value $R_{i,j}$ in measurement point (i,j) can be obtained by the following formula (3).

$$R_{i,j} = \epsilon_{0k}/\epsilon_{i,j} \qquad (3)$$

Accordingly, even when an object is inadequately compressed whereby causing the strain of the reference region in lateral direction to be uneven, since the compression can be assumed to be even within the respective segmented regions it is possible to obtain the index value with high accuracy with respect to every segmented region. As a result, the index value can be accurately obtained as the whole indexed elastic image.

While it is described as taking the segmented regions comparatively wide in lateral direction in the explanation above, index value $R_{i,j}$ in measurement point (i,j) may be obtained using the following formula (4) by setting the segmented regions independently with respect to each line.

$$R_{i,j} = \epsilon_{0i}/\epsilon_{i,j} \qquad (4)$$

The invention claimed is:

1. An ultrasonic diagnostic apparatus comprising:
an ultrasonic probe configured to transmit/receive ultrasonic waves/echo signals to/from tissue of an object to be examined; and
an ultrasonic diagnostic system constructed at least in part of circuitry, memory and a display, to perform operations to:
provide driving ultrasonic pulses to the ultrasonic probe for the transmission of the ultrasonic waves;
amplify received echo signals from the ultrasonic probe;
generate tomographic data based on the amplified received echo signals;
convert the tomographic data to a displaying tomographic image based on a gray-scale;
obtain an RF signal group corresponding to a scanning area of ultrasonic beams for a portion of a plurality of frames of the amplified received echo signals;
perform correlation processes on a selected pair of frames of different compression quantity, and generate displacement frame data by measuring the displacement of respective measurement points in the scanned area;
calculate strain/elasticity modulus using the displacement frame data;
generate elastic image data based on the strain or elasticity modulus;
convert the generated elastic image data to a displaying elastic image based on a color-scale;
switch at least one of the displaying tomographic image or the displaying elastic image;
display the at least one of the displaying tomographic image or the displaying elastic image from the switch; and
control data transmission from a transmitting circuit to the display by an interface;
select a reference region on the at least one of the displaying tomographic image or the displaying elastic image, and
calculate an indexed elastic image frame data based on formed gradation of ratio between the strain of the respective measurement points and the strain of the reference region, so as to eliminate the influence of compression quantity of the indexed elastic image frame data,
wherein the display displays an indexed elastic image based on the indexed elastic image frame data.

* * * * *